US007214023B2

(12) United States Patent
Sato et al.

(10) Patent No.: US 7,214,023 B2
(45) Date of Patent: May 8, 2007

(54) AUTOMATIC STORAGE SYSTEM

(75) Inventors: Koji Sato, Hitachinaka (JP); Sadato Igarashi, Hitachinaka (JP)

(73) Assignee: Hitachi Koki Co., Ltd., Tokyo (JP)

( * ) Notice: Subject to any disclaimer, the term of this patent is extended or adjusted under 35 U.S.C. 154(b) by 404 days.

(21) Appl. No.: 10/638,324

(22) Filed: Aug. 12, 2003

(65) Prior Publication Data

US 2004/0037680 A1    Feb. 26, 2004

(30) Foreign Application Priority Data

Aug. 21, 2002    (JP)    ............... P2002-241131

(51) Int. Cl.
*G01N 15/06*    (2006.01)
(52) U.S. Cl. ..................................... 414/281
(58) Field of Classification Search .......... 414/281, 414/266, 273
See application file for complete search history.

(56) References Cited

U.S. PATENT DOCUMENTS

| | | | | |
|---|---|---|---|---|
| 3,575,692 A | * | 4/1971 | Gilford ..................... 422/65 |
| 3,687,632 A | * | 8/1972 | Natelson ................. 73/864.25 |
| 4,678,390 A | * | 7/1987 | Bonneton et al. ............ 414/282 |
| 4,678,894 A | * | 7/1987 | Shafer ..................... 235/375 |
| 5,669,221 A | * | 9/1997 | LeBleu et al. ................ 62/92 |
| 5,998,799 A | * | 12/1999 | Cremer et al. ............ 250/504 R |
| 6,068,437 A | | 5/2000 | Boje et al. |
| 6,096,561 A | * | 8/2000 | Tayi ..................... 436/518 |
| 6,357,983 B1 | | 3/2002 | Junca |
| 6,478,524 B1 | * | 11/2002 | Malin ..................... 414/283 |
| 6,700,734 B2 | * | 3/2004 | Satoh ..................... 360/92 |
| 6,890,485 B1 | * | 5/2005 | Stylli et al. .............. 422/68.1 |
| 6,919,044 B1 | * | 7/2005 | Shibata et al. ............. 422/63 |
| 2001/0030492 A1 | * | 10/2001 | Branz et al. ............. 312/236 |

FOREIGN PATENT DOCUMENTS

| | | |
|---|---|---|
| EP | 0 846 636 A1 | 6/1998 |
| JP | 2002-205804 | 7/2002 |
| JP | 2002-234601 | 8/2002 |

OTHER PUBLICATIONS

European Search Report dated Dec. 2, 2003.

* cited by examiner

*Primary Examiner*—Charles A. Fox
(74) *Attorney, Agent, or Firm*—McGuireWoods LLP

(57) ABSTRACT

First and second shelf sections are positioned side by side in an outer frame. A transfer section is movable along a linear space defined between the first and second shelf sections. The transfer section includes a movable base and a rack pull-out mechanism provided on the movable base for pulling out each rack stored in the shelf sections. The base has a mounting area beside the rack pull-out mechanism for mounting thereon a receptible rack. A repacking mechanism including a picker mechanism is provided on the transfer section for moving a sample container from the rack on the rack pull-out mechanism to the receptible rack on the mounting area.

20 Claims, 5 Drawing Sheets

AUTOMATIC STORAGE SYSTEM

BACKGROUND OF THE INVENTION

The present invention relates to an automatic storage system used in the field of medical science, pharmacy, agriculture, clinical medicine, and bio-technology. More particularly, the invention relates to such automatic storage system for storing a plurality of sample containers and picking up a selected sample container(s).

As a result of technological innovation in various fields such as medical science, pharmacy, agriculture, clinical medicine, and bio-technology, various kinds of testing samples must be investigated. To this effect, greater numbers of sample containers accumulating therein various kind of testing samples such as blood, ferment, gene, a chemical compound, a chemical reagent must be stored and picked-up for the investigation.

A conventional automatic storage system is shown in FIGS. 8 and 9. The storage system includes a storage section 110 for storing a plurality of sample containers 2 accommodated in a plurality of racks 3, a transfer section 120 for picking-up a rack 3 from the storage section 110, and a repacking section 126 for picking up one or several sample containers from the rack 3 or accommodating other sample container(s) into the rack 3. The storage system also includes a control section 130 for controlling operation of the storage section 110, the transfer section 120 and the repacking section 126.

In the storage section 110, a plurality of shelves 114 area arrayed side by side, and these shelves 114 are circularly moved as shown by an arrow F in FIG. 9. In each shelf 114, a plurality of racks 3 are vertically arrayed and held in positions. The storage section 110 has an elongated configuration.

The transfer section 120 is positioned at one longitudinal end of the storage section 110. The transfer section 120 includes an arm robot and a belt conveyer movable in both horizontal and vertical direction as shown by arrows G and H for picking up a selected one of the racks 3 from a selected one of the shelf 114 moved and stopped beside the transfer section 120 and for transferring the selected rack 3 to the repacking section 126. The transfer section 120 is also adapted for transferring the rack 3 from the repacking section 126 to the storage section 110.

The repacking section 126 is positioned beside the transfer section 120 at a position opposite to the storage section 110. The repacking section 126 includes a picker mechanism 129 and a stand 122 on which a receptible rack 4 is to be mounted. The picker mechanism 129 is adapted for picking up a selected sample container 2 from the rack 3 and accommodates the selected sample container 2 into the receptible rack 4. The repacking section 126 is also adapted for accommodating a sample container 2 from the receptible rack 4 to the rack 3.

The control section 130 stores therein data indicative of position of each sample container 2 and each rack 3, and transmits command signal to the storage section 110, the transfer section 120 and the repacking section 126. More specifically, when a specific sample container 2 is input through the control section 130, the storage section 110 performs circular movement so that a specific rack 3 accommodating therein the specific sample container 2 can be positioned in confrontation with the transfer section 120 based on the position data of the racks and the sample containers. Then, the transfer section 120 picks up the specific rack 3 from the storage section 110, and transfers the specific rack 3 to the repacking section 126 where the picker mechanism 129 picks-up the specific sample container 2 from the specific rack 3, and accommodates the specific sample container 2 into the receptible rack 4 mounted on the case stand 122. Then the specific rack 3 is returned to the storage section 110 by the transfer section 120. This operation is repeatedly performed so that desired sample containers 2 can be accommodated into the receptible rack 4.

The above described conventional automatic storage system has been developed from an industrial automatic storage house, and is extremely large occupying an entire space of the storage house. However, such system is too large in the field of medical science, pharmacy, agriculture, clinical medicine, and bio-technology except for a storage of chemical compounds of pharmaceutical industry company. Therefore, a compact storage system has been demanded.

Further, in the conventional system, since the storage section 110, the transfer section 120 and the repacking section 126 are separated from each other, each rack must be moved from the storage section 110 to the repacking section 126 each time a desired sample container is picked up. This takes a long period of time.

Further, due to repeated picking-up and storing operations, sample containers 2 may be scattered over various racks 3. Therefore, the sample containers must be in trim order in the reduced numbers of racks 3. For the proper arrangement of the sample containers, an operator must be manually repack the sample containers among the racks in the storage section 110. However in this case, the position data of the sample containers and racks may be destroyed.

In the conventional automatic repacking operation, the storage section 110 must perform circular movement until the desired rack 3 is brought into confrontation with the transfer section 120, and this circular movement must be performed each time the desired sample container must be picked up by the picker mechanism 129 from each rack 3 while the identical receptible rack 4 remains on the stand 122. Such process is extremely complicated.

Japanese patent application Publication No.2002-205804 discloses storage shelves positioned side by side, and an automatic pick-up device runs between the storage shelves for picking up a desired rack from the shelf, and for transferring the picked up rack to a transfer box outside of the shelves. Further, an external station is positioned for picking up a container or a test tube accommodated in the rack.

Japanese patent application Publication no. 2002-234601 discloses a pair of shelves each circularly moved in a vertical direction. A rail extends through a space between the pair of shelves, and a transfer unit runs along the rail.

SUMMARY OF THE INVENTION

It is an object of the present invention to overcome the above-described problems and to provide a compact automatic storage system capable of rapidly repacking sample containers from one rack to another rack, or capable of rapidly relocating sample containers in the identical rack.

These and other objects of the present invention will be attained by an automatic storage system for storing sample containers held in racks including an outer frame, a first shelf section and a second shelf section, a transfer section, a repacking mechanism, and a control section. The first and second shelf sections are positioned in the outer frame for storing a plurality of racks in which a plurality of sample containers are installable. The first and second shelf sections are positioned side by side with a space therebetween. The transfer section is movable in the space and including a rack pull-out mechanism and a base. The rack pull-out mechanism is adapted for pulling out the rack from either one of the first and second shelf sections, maintaining the pulled-out rack on the rack pull-out mechanism and returning the pulled-out rack to one of the first and second shelf sections. The base is movable in a horizontal direction and a vertical direction in the space. The rack pullout mechanism is set on the base. The base includes a mounting area on which a receptible rack is mountable. The repacking mechanism is provided on the transfer section for moving at least one sample container from a first position to a second position. The control section is connected to the transfer section and the repacking mechanism for managing operation thereof and managing position data of the racks and sample containers.

DETAILED DESCRIPTION OF THE PREFERRED EMBODIMENTS

Figure 1:
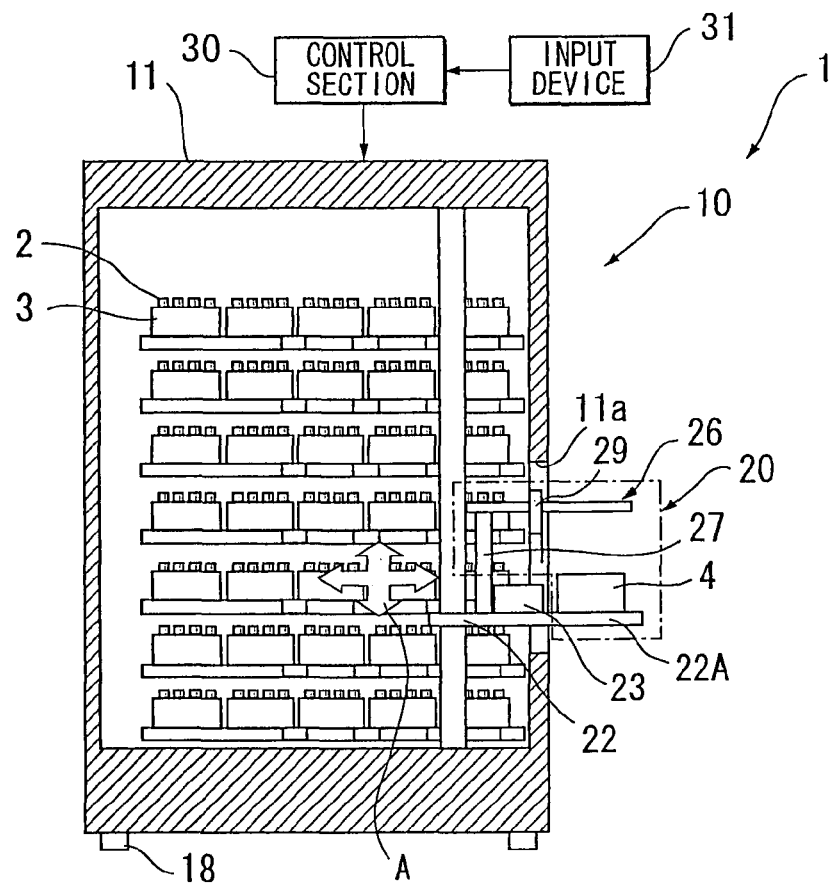
FIG. 1 is a front view showing an automatic storage system in which its transfer section is in its stand-by position according to one embodiment of the present invention.

An automatic storage system according to one embodiment of the present invention will be described with reference to FIGS. 1 through 7. A plurality of box shaped racks 3 and a plurality of box shaped receptible racks 4 are used. Each rack 3 and receptible rack 4 is formed with a plurality of holes for accommodating therein a plurality of sample containers 2. The receptible racks 4 is adapted for collecting at least one sample container 2 from the rack 3.

Bar code is formed at an outer vertical surface of each rack 3 for identification. Further, bar code is also formed at a bottom of each sample container 2 for identification. The bar code also identifies a content accumulated in the sample container 2.

The automatic storage system 1 includes a storage section 10 and a control section 30 connected thereto. The storage section 10 includes a box-shaped frame 11. Casters 18 are connected to a bottom wall of the frame 11 for moving the storage section 10 to a desired site. A take out hole 11a is formed at a side wall of the frame 11.

Figure 2:
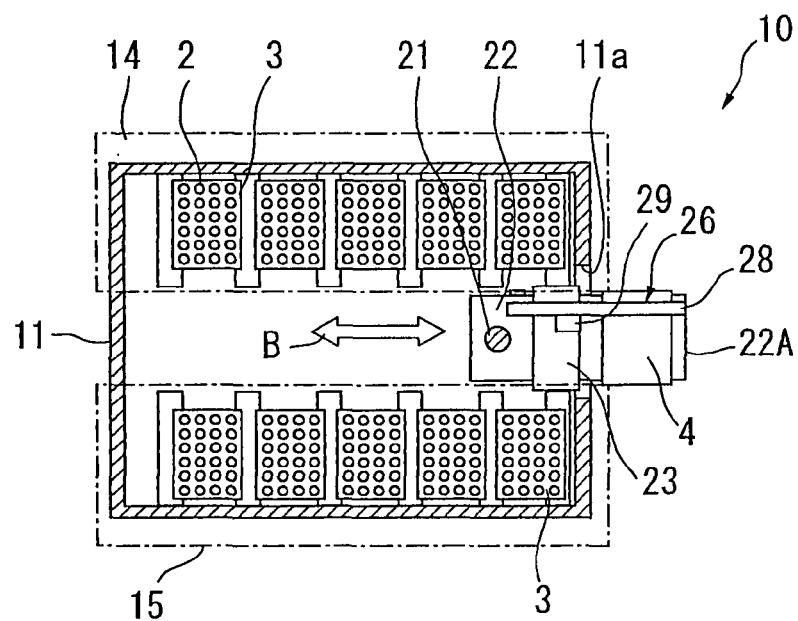
FIG. 2 is a cross-sectional plan view showing the automatic storage system in which its transfer section is in its stand-by position according to the embodiment.

As shown in FIG. 2, first and second shelf sections 14, 15 are installed in the storage section 10 in a juxtaposed fashion for storing therein the plurality of racks 3. The first shelf section 14 is installed at an inner rear vertical wall of the frame 11, and a second shelf section 15 is installed at inner front vertical walls thereof. As shown in FIG. 2, each shelf section 14, 15 has a plurality of shelves extending horizontally and in parallel with each other so as to mount a plurality of racks 3 in their upstanding orientation.

At a linear space between the first and second shelf sections 14 and 15, a transfer mechanism 20 is provided which is movable in vertical and horizontal directions as shown by arrows A and B in FIGS. 1 and 2. The transfer mechanism 20 includes a vertical rod 21 movable in horizontal direction, a base 22 extending horizontally and movable in vertical direction along the vertical rod 21, and a rack pull-out mechanism 23 provided on the base 22. The rack pull-out mechanism 23 is adapted for pulling out a desired rack 3 from the shelf, or returning the pulled out rack 3 to a desired position of a desired shelf. To this effect, the rack pull-out mechanism 23 includes a slide arm (not shown) movable in frontward/rearward direction as indicated by arrow C in FIG. 4 and in a vertical direction, and accessible to a position immediately below a bottom of a desired racks 3 stored at any one of the shelves in the first and second self sections 14,15.

The base 22 has a mounting area 22A on which a receptible rack 4 is to be mounted. The mounting area 22A can be positioned outside of the frame 11 through the side opening 11a when the transfer section 20 is at its stand-by position for facilitating set up of the receptible rack 4 onto the mounting area 22A from outside of the frame 11.

A repacking mechanism 26 is provided on the transfer mechanism 20. That is, the repacking mechanism 26 includes a vertical support rod 27 extending from the base 22 and movable in the frontward/rearward direction C, a horizontal rod 28 extending from the vertical support rod 27, and a picker mechanism 29 movable along the horizontal rod 27. The picker mechanism 28 is vertically movable and includes a plurality of hand arms for holding a desired one of the sample containers 2. The horizontal rod 28 extends over the rack pull-out mechanisms 23 and over the receptible rack mounting area 22A so that the picker mechanism 29 can access to the sample containers 2 held on the rack 3 on the rack pull-out mechanism 23 and to the receptible rack 4 on the mounting area 22A.

The control section 30 includes a ROM (not shown) storing various operation programs for the transfer mechanism 20 and the repacking mechanism 26. The control section 30 also includes a memory region (not shown) storing data of position of each sample container 2 with respect to the rack 3, data of content of each sample container 2, and data of position of each rack 3. A bar code reader (not shown) is connected to the control section 30 for reading bar codes of the racks 3 and sample containers 2 as an initial setting. An input device 31 is connected to the control section 30 for inputting various data.

Setting operation for setting the sample containers 2 into the racks 3 and for setting the racks 3 into the shelf sections 14 and 15 will be described. First, data of each sample containers 2 and data of position of each sample container 2 with respect to a rack 3 are read by the bar code reader (not shown), and these data are stored in the memory region of the control section 30.

Then, each rack 3 carrying the sample containers 2 is mounted on the rack pull-out mechanism 23 so as to set the rack 3 to one of the shelf sections 14, 15. Then, the position of each rack relative to the shelves is input through the input device 31, and the positions are stored in the memory region.

With this process, the racks 3 can be set at any position of the shelves of the first and second shelf sections 14 and 15, and therefore, great numbers of racks 3 can be promptly stored on the shelf sections 14 and 15. Further, positions of all sample containers 2 relative to the racks 3 and positions of the racks 3 can be recognized by the control section 30.

Figure 3:
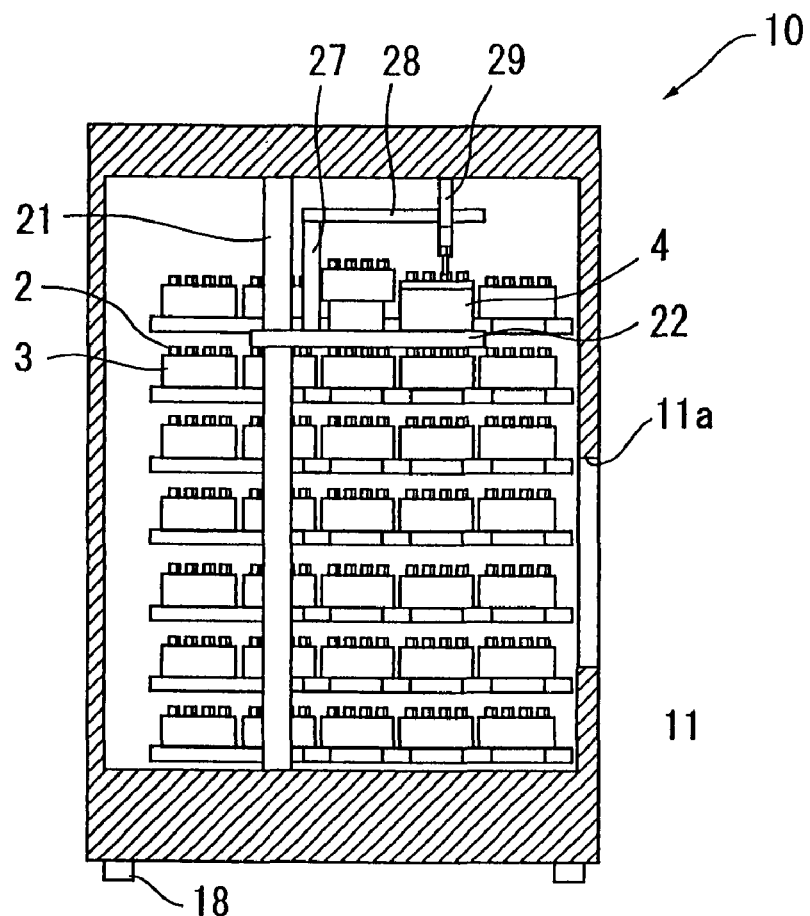
FIG. 3 is a side view showing the automatic storage system in which the transfer section is moved according to the embodiment.
Figure 4:
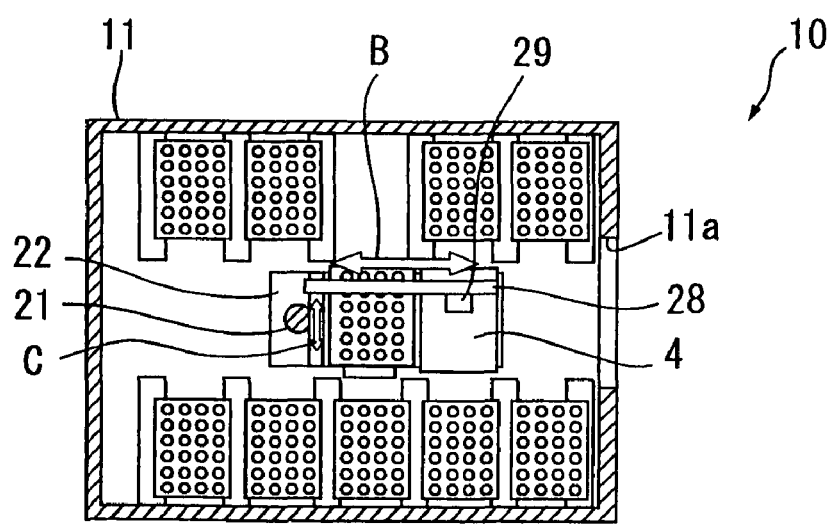
FIG. 4 is a cross-sectional plan view showing the automatic storage system in which the transfer section is moved according to the embodiment.
Figure 5:
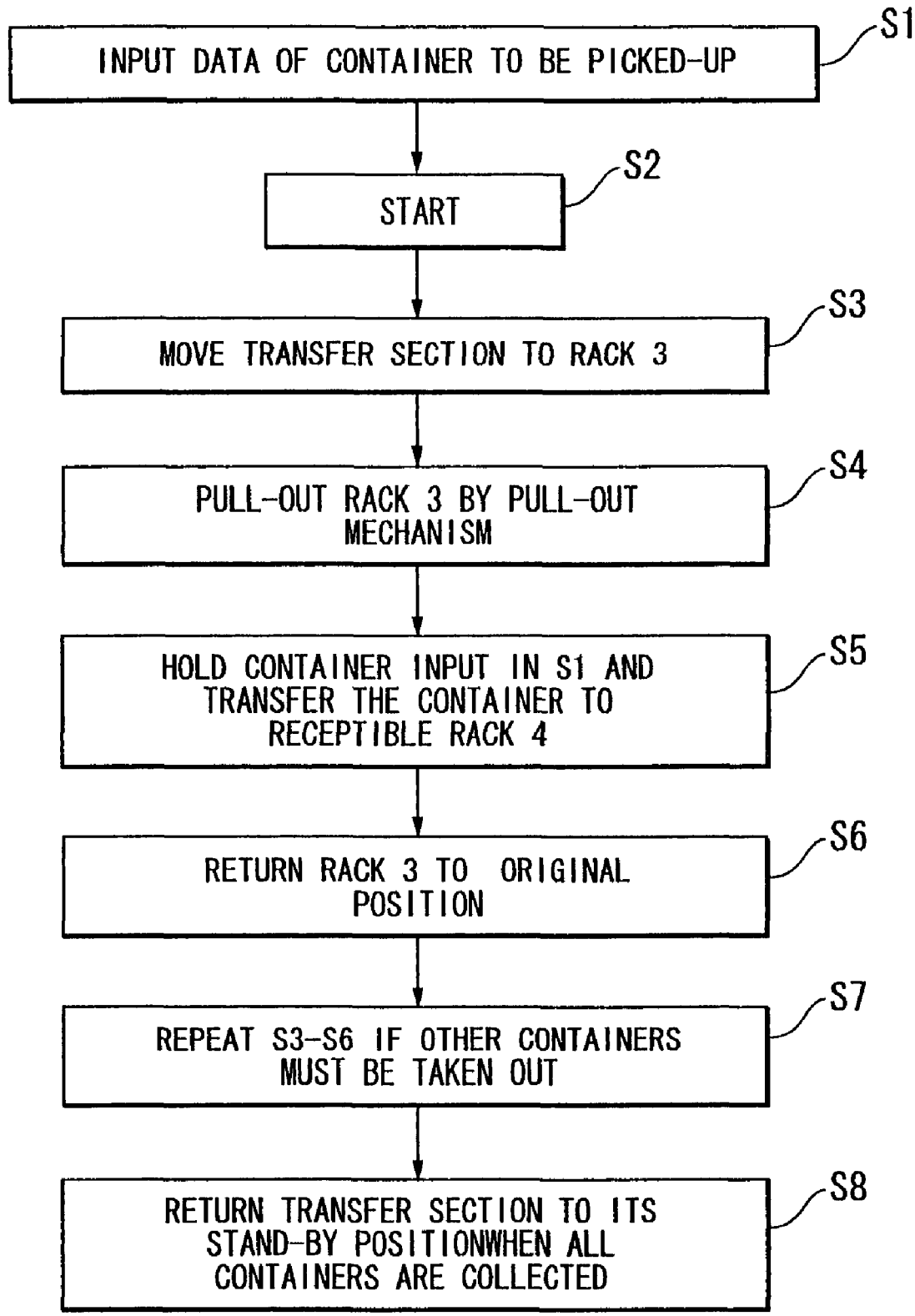
FIG. 5 is a flow chart showing a process of repacking sample containers from rack(s) to a receptible rack according to the embodiment.

Next, a process for picking up the desired sample container 2 will be described with reference to FIGS. 1, 2 and 5. As described above, in the stand-by position of the transfer section 20, the mounting area 22A of the base 22 protrudes out of the frame 11 through the side opening 11a. In this protruding state of the base 22, a receptible rack 4 is mounted on the mounting area 22A of the base 22 from outside of the frame 11, and data of the sample container 2 to be picked up is input through the input device 31 connected to the control section 30 (S1), and then the routine is started (S2). Then, as shown in FIGS. 3 and 4, the base 22 of the transfer mechanism 20 is moved to a position adjacent to the rack 3 which holds the sample container 2 input in S1 (S3). Then, the rack pull-out mechanism 23 pulls out the rack 3. That is, the slide arm is horizontally moved below the rack 3, and then is moved slightly upwardly, so that the rack 3 is slightly moved away from the shelf. Then, the slide arm is retracted to move the rack 3 above the base 22 (S4).

Then, the picker mechanism 29 holds the desired sample container 2 in the rack 3, and transfers the desired sample container 2 to the receptible rack 4 (S5). Upon completion of the transfer, the specific rack 3 is returned to its original position by the rack pull-out mechanism 23 (S6). If a plurality of sample containers 2 accommodated in racks different from each other are to be picked up, the above process from S3 to S6 are repeatedly executed (S7). When all desired sample containers are repacked into the receptible rack 4, the transfer section 20 is moved to its stand-by position as shown in FIGS. 1 and 2 (S8).

Figure 8:
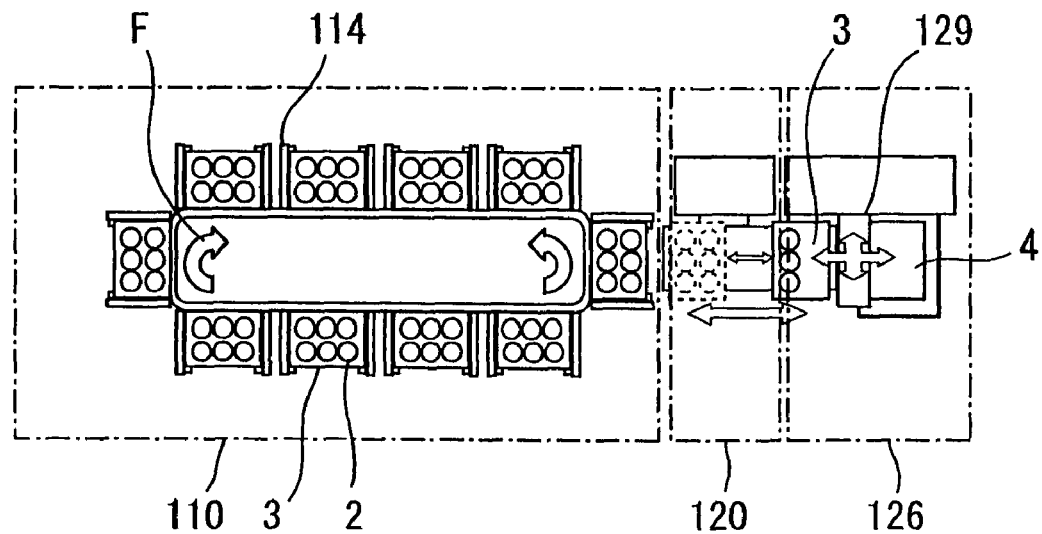
FIG. 8 is a schematic plan view showing a conventional automatic storage system.
Figure 9:
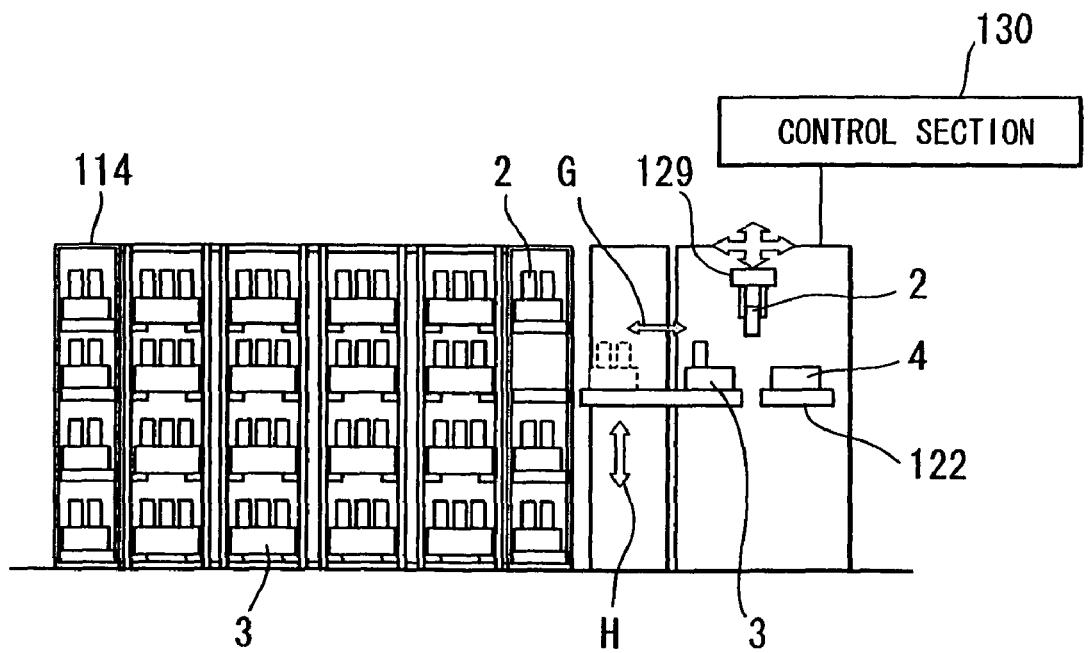
FIG. 9 is a front view showing the conventional automatic storage system.

In the above-described arrangement, since the rack pull-out mechanism 23 and the picker mechanism 29 of the repacking mechanism 26 are provided on the transfer mechanism 20, it becomes possible to perform repacking operation between the rack 3 and the receptible rack 4 within a space defined between the first and second shelf sections 14 and 15. In other words, it is unnecessary to carry these racks to a different repacking region as seen in the conventional system shown in FIGS. 8 and 9. Consequently, time saving repacking operation can result. Further, since the storage section 10, the transfer section 20 and the repacking section 26 are all disposed in the frame 11, compact system can be provided.

Figure 6:
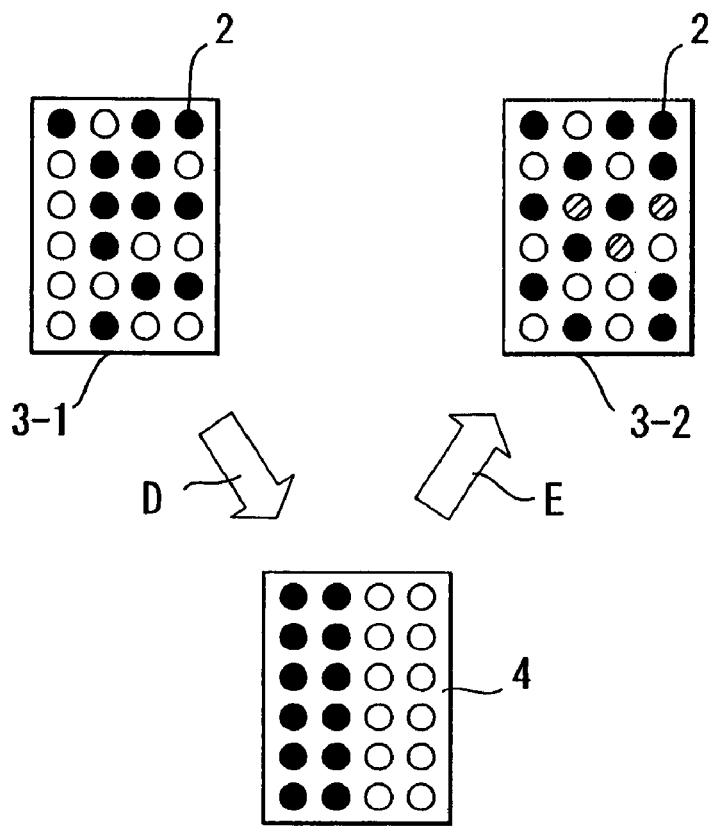
FIG. 6 is a cross-sectional plan view for description of repacking sample containers from one rack to another rack through a receptible rack according to the embodiment.

FIG. 6 shows a process of repacking the sample containers from a rack 3-1 to a rack 3-2 through a receptible rack 4. In FIG. 6, black circles imply that the sample containers are positioned, white circles imply that no sample container is positioned, and hatching circles imply that sample containers have already been positioned. First, a rack 3-1 is pulled out to a position above the base 22 by means of the rack pull-out mechanisms 23. Then, the picker mechanism 29 moves over the racks 3-1 and the receptible rack 4 so as to shift all sample containers 2 in the rack 3-1 to the receptible rack 4 as shown by arrow D in FIG. 6.

Then, the vacant rack 3-1 is returned to its original position by the rack pull-out mechanism 23. Alternatively, the vacant rack 3-1 can be collected into a rack collection box (not shown). Then, the transfer section 20 moves to a position in front of a vacant rack 3-2 while carrying the receptible rack 4 in which all samples from the rack 3-1 have been packed, and the rack 3-2 is pulled out by the rack pull-out mechanism 23. Then, the picker mechanism 29 moves over the racks 3-2 and the receptible rack 4 so as to shift all sample containers 2 in the receptible rack 4 to the rack 3-2 as shown by arrow E in FIG. 6.

Figure 7:
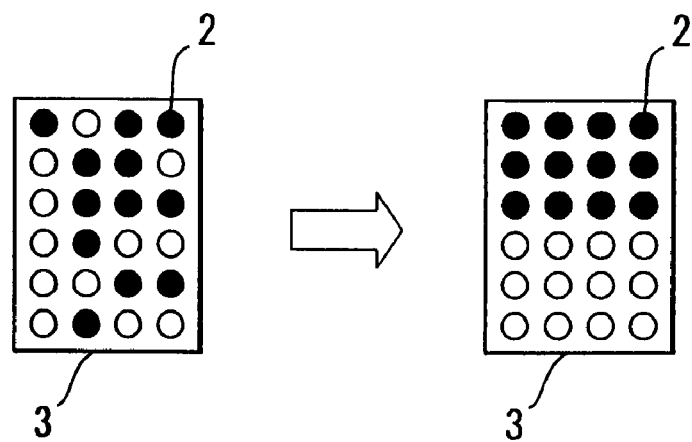
FIG. 7 is a view for description of relocating all sample containers in good order in an identical rack according to the embodiment.

FIG. 7 shows relocations of the sample containers 2 in the identical rack 3 for proper arrangement of the containers 2. Prior to the relocations, the sample containers 2 are located in a scattered manner in the rack 3. By operating the rack pull-out mechanism 23 and by operating the picker mechanism 29, the sample containers 2 can be relocated in a tight fashion. Consequently, space in the storage section 10 can be effectively utilized.

In the present embodiment, sample containers 2 can be automatically stored into the storage section 10. First, the bar codes of the sample containers 2 are read by the bar code reader (not shown), and the sample containers 2 to be stored are set in the receptible rack 4 held on the mounting area 22A. Then, storage of the sample containers 2 is input into the control section 30 through the input device 31. Because the control section 30 recognizes the setting manner of the sample containers of the various racks 3, the control section 30 selects a suitable rack 3 capable of setting additional sample containers 2 and already stored in one of the first and second shelf sections 14 and 15. The selected rack 3 is then pulled out by the rack pull-out mechanism 23, and the sample containers 2 are transferred from the receptible rack 4 to the selected rack 3 by the picker mechanism 29. Thus, the sample containers can be automatically stored in the proper rack.

While the invention has been described in detail with reference to specific embodiments thereof, it would be apparent to those skilled in the art that various changes and modifications may be made therein without departing from the spirit and scope of the invention.

For example, a temperature control device can be installed in the box-shaped frame 11 if the testing samples in the containers 2 require temperature control.

Further, the frame 11 can be formed of punched metal plate where a plurality of perforations are penetratingly formed throughout the thickness so as to provide free ventilation between inner and outer space of the storage section 10. Thus, temperature control with respect to sample containers 2 stored in the storage section 10 can be performed through the perforations even if the storage section 10 is not provided with temperature control device, as long as the storage section 10 is installed in a room equipped with an air conditioning system. Accordingly, extra space for installing the temperature control device is not required in the storage section 10, to thus increase installation space for the sample containers 2.

Further, in the above-described embodiment, the slide arm of each rack pull-out mechanisms 23, 24 is movable in vertical direction as well as frontward/rearward direction for an access to the position immediately below the bottom of the desired racks 3 stored at the shelf. However, vertical movement of the slide arm can be eliminated by providing a retractable pawl on the upper surface of the slide arm. The retractable pawl retracts when the pawl is moved past the bottom surface of the rack, and projects when the pawl has finished passing so as to engage a rear vertical wall of the rack.

What is claimed is:

1. An automatic storage system for storing sample containers held in racks, comprising:
   an outer frame;
   a first shelf section and a second shelf section positioned in the outer frame to store a plurality of racks in which a plurality of sample containers are installable, the first shelf section and the second shelf section being positioned side by side with a space therebetween;
   a transfer section movable in the space, and comprising:
      a rack pull-out mechanism to pull out a rack from either one of the first and second shelf sections, maintaining the pulled-out rack on the rack pull-out mechanism and returning the pulled-out rack to one of the first and second shelf sections, and
      a base movable in a horizontal direction and a vertical direction in the space and on which the rack pullout mechanism is set, the base also including a mounting area on which a receptible rack is mountable;
   a repacking mechanism supported by a vertical support rod having one end attached to the base and provided on the transfer section for moving at least one sample container from a first position to a second position; and
   a control section connected to the transfer section and the repacking mechanism to manage operation thereof and to manage position data of the racks and sample containers.

2. The automatic storage system as claimed in claim 1, wherein the first position is located in the rack and a second position is located in the receptible rack.

3. The automatic storage system as claimed in claim 1, wherein the first and second position is located in an identical rack.

4. The automatic storage system as claimed in claim 1, wherein the outer frame has a side wall formed with a side opening through which at least the mounting area of the base is protrudable out of the side wall.

5. The automatic storage system as claimed in claim 1, wherein the transfer section comprises a horizontally moving member movable along the space, the base being vertically movable along the horizontally moving member.

6. The automatic storage system as claimed in claim 5, wherein the repacking mechanism comprises:
   a support rod positioned on the base and movable in a frontward/rearward direction of the frame, the support rod extending in the lengthwise direction of the space over the pull-out mechanism and the mounting area of the base; and
   a picker mechanism supported on the support rod and movable therealong, the picker mechanism being also movable in the vertical direction and having an arm for holding the sample container supported by the rack.

7. The automatic storage system as claimed in claim 1, wherein each rack is formed with a bar code for identification, the automatic storage system further comprising:
   a bar code reader connected to the control section for reading each bar code and transmitting data of position of each rack on the first and second shelf sections.

8. The automatic storage system as claimed in claim 1, further comprising a temperature control device disposed in the outer frame.

9. The automatic storage system as claimed in claim 1, wherein the outer frame is formed with a plurality of venting perforations.

10. The automatic storage system as claimed in claim 1, further comprising casters provided at a bottom of the outer frame.

11. The automatic storage system of claim 1, wherein the outer frame comprises four sides with at least three of the four sides substantially closed and a fourth side of the four sides being partially open to permit the mounting area of the base to protrude outside the fourth side.

12. The automatic storage system of claim 11, wherein the outer frame include casters to permit movement of the outer frame and the first and the second shelf sections with the space therebetween.

13. The automatic storage system of claim 11, wherein at least one of the four sides is perforated.

14. The automatic storage system of claim 1, wherein the plurality of racks and the receptible rack include a plurality of holes to receive the sample containers.

15. The automatic storage system of claim 14, wherein the position data of the sample containers includes data denoting a hole associated with a particular sample container within the receptible rack or the plurality of racks.

16. An automatic storage system for storing sample containers held in racks, comprising:
   an outer frame forming a substantially closed box-shaped enclosure except for an opening in one wall of the enclosure;
   a first shelf section and a second shelf section fixedly positioned within the outer frame to store a plurality of racks in which a plurality of sample containers are installable, the first shelf section and the second shelf section being positioned side by side with a space therebetween;
   a transfer section movable in the space, and comprising:
      a rack pull-out mechanism to pull out a rack from either one of the first and second shelf sections and to maintain the pulled-out rack on the rack pull-out mechanism and to return the pulled-out rack to one of the first and second shelf sections, and
      a base movable in a horizontal direction and a vertical direction in the space and on which the rack pullout mechanism is set, the base also including a mounting area on which a receptible rack is mountable;
   a repacking mechanism supported by a vertical support rod having one end attached to the base and provided on the transfer section to move at least one sample container from a first position to a second position; and
   a control section connected to the transfer section and the repacking mechanism to manage operation thereof and to manage position data of the racks and sample containers, wherein the position data uniquely defines specific positions within the racks and maintains an association of the sample containers with a specific position.

17. The automatic storage system of claim 16, wherein the outer frame has a side wall formed with a side opening through which at least the mounting area of the base is protrudable out of the side wall.

18. The automatic storage system as claimed in claim 16, wherein the outer frame is formed with a plurality of venting perforations.

19. An automatic storage system for storing sample containers held in racks, a first rack having a first code for identification and each sample container held in the first rack has a second code for identification, comprising:
   a storage section; and
   a control section connected thereto;
   said control section including a memory region for storing code data and position data; and said storage section including:

a first shelf section and a second shelf section positioned side by side with an aisle way;

a transfer section having a base movable horizontally along the aisle way and vertically on the aisle way;

a repacking mechanism supported by a vertical support rod having one end attached to the base and provided on the transfer section for moving at least one sample container from a first position to a second position; and a rack transfer mechanism mounted on the base and movable from the aisle way to each of the shelf sections to set a rack on the base to either one of the first and second shelf sections, wherein setting of the first rack into one of the shelf sections is performed such that the second code of the sample container and position data of each sample container with respect to the first rack are read and stored in the memory region of the control section, the first rack is mounted on the transfer section and is set to one of the shelf sections, and the first code of the first rack and position data of the first rack relative to the shelf sections are stored in the memory region of the control section.

20. An automatic storage system as claimed in claim 19 wherein the repacking mechanism further comprises:

a picker mechanism having an arm vertically and horizontally movable to hold a desired one of sample containers;

wherein repacking a first sample container held in the first rack is performed such that a receptible rack is mounted on the base and the second code of the first sample container is stored in the memory region of the control section, the base is moved to a position adjacent to the first rack which holds the first sample container, the rack transfer mechanism pulls out the first rack having the first sample container, and the picker mechanism holds and transfers the first sample container to the receptible rack.

* * * * *